United States Patent [19]

Dell et al.

[11] Patent Number: 4,491,589

[45] Date of Patent: Jan. 1, 1985

[54] AMINO ACID SOLUTIONS FOR PARENTERAL NUTRITION AND METHODS OF FORMULATION AND USE

[75] Inventors: Ralph B. Dell, New York, N.Y.; Robert W. Winters, Summit, N.J.; William C. Heird, New York, N.Y.

[73] Assignee: The Trustees of Columbia University in the City of New York, New York, N.Y.

[21] Appl. No.: 487,409

[22] Filed: Apr. 29, 1983

Related U.S. Application Data

[63] Continuation-in-part of Ser. No. 378,743, May 17, 1982, abandoned.

[51] Int. Cl.³ .................... A61K 31/40; A61K 31/195
[52] U.S. Cl. ...................................... 424/274; 424/319
[58] Field of Search ................................ 424/319, 274

[56] References Cited

U.S. PATENT DOCUMENTS

| | | | |
|---|---|---|---|
| 2,411,897 | 12/1946 | Sayhum | 424/319 |
| 2,662,046 | 12/1953 | Howe | 424/319 |
| 3,152,955 | 10/1964 | Gow et al. | 424/319 |
| 4,279,917 | 7/1981 | Takami | 424/319 |
| 4,357,343 | 11/1982 | Madsen | 424/319 |

*Primary Examiner*—Stanley J. Friedman
*Attorney, Agent, or Firm*—John P. White

[57] ABSTRACT

For parenteral nutrition, an aqueous L-amino acid solution having an amino acid content consisting essentially of essential and non-essential amino acids in proportions for producing and maintaining, in a subject to whom the same is administered, a steady-state plasma amino acid pattern within established ranges for the normal subject's post-prandial plasma amino acid pattern.

22 Claims, No Drawings

AMINO ACID SOLUTIONS FOR PARENTERAL NUTRITION AND METHODS OF FORMULATION AND USE

The invention described herein was made in the course of work under grant No. 5 R01 HD-08434 from the National Institutes of Health, Department of Health and Human Services.

BACKGROUND OF THE INVENTION

This is a continuation-in-part of U.S. application Ser. No. 378,743, filed May 17, 1982, now abandoned.

The present invention relates to amino acid solutions for administration to patients who require parenteral nutrition, and to methods of formulating and using such solutions. More particularly, the invention relates to parenteral solutions containing L-amino acids in proportions for promoting anabolism in pediatric patients to attain growth, and in depleted adult patients to attain repletion of lean body mass, as well as to methods of formulating and using the same.

It is recognized that parenteral nutrition, especially total parenteral nutrition (TPN), also called "hyperalimentation," can provide dramatic or even life saving nutritional support for patients with a wide variety of illnesses, varying from infants with surgically reparable anomalies of the gastrointestinal tract or with chronic intractable diarrhea to adults with short gut syndromes, inflammatory bowel disease and even certain patients with advanced malignant disease. This technique as usually practiced involves the insertion of a plastic catheter into the central venous circulation and the provision of all nutrients in their most elemental chemical form by this route, although the nutritional regimen may be delivered through a peripheral vein under some circumstances. As is well known, the supply of amino acids in such manner constitutes an important aspect of parenteral nutrition.

Of the total population of patients who are candidates for TPN, the fundamental intent in the majority is to support anabolism—i.e., somatic growth (in infants) or replenishment or "regrowth" of previously depleted lean body mass, which has occurred due to a failure of the oral intake to provide an adequate nutritional intake in the face of an accelerated rate of catabolism of lean body mass due to an on-going stress. The purpose of parenteral nutrition and hence the nutritional regimen in these groups of patients differ from patients who have specific defined disorders in the metabolism of given amino acids, such as those with hepatic encephalopathy, or those with acute renal failure in whom a parenteral nutritional regimen delivering only the essential amino acids is the preferred nutritional treatment.

Extensive studies have shown that all currently available amino acid solutions used as nitrogen sources in parenteral nutritional regimens in infants are associated with specific and significant abnormalities in the plasma concentration of several of the amino acids. Depending upon the individual solutions, the aberrations consist of elevated plasma levels of some amino acids and depressed levels of others compared to a "normal" standard.

Such aberrations in the plasma cell into question both the safety and the efficacy of the available amino acid solutions because known information, especially from the study of certain inborn errors of metabolism, inferentially indicates that hyperaminoacidemia may be detrimental to the function and/or development of the nervous system, whereas hypoaminoacidemia may signify nutritional inadequacy of the amino acid solution. Also pertinent is the concept of amino acid imbalance which stresses the adverse consequences (in the plasma and in the tissues, especially in the brain) of disturbing the pattern of amino acids in the intake, although it will be appreciated that disturbing the intake is not always associated with adverse consequences. For example, in phenylketonuria, maple syrup disease and other abnormal conditions, primary therapy consists of reducing phenylalanine, branched chain amino acids, etc., in the diet such that the intake is disturbed. One of the resulting consequences of this is more normal plasma amino acid concentrations and patterns. Likewise in parenteral nutrition, wherein the actions of the gastrointestinal and hepatic functions are bypassed, it is extremely important to consider the intake of all nutrients, including amino acids.

For all of these reasons, an amino acid solution formulated for parenteral nutrition that would result in "normal" concentrations for all amino acids as well as a normal pattern and normal interrelationships (molar ratios) between the various amino acids in plasma would be desirable. It would be especially desirable to provide such solutions that supply amino acids in appropriate proportions for growth in infants and depleted adults.

SUMMARY OF THE INVENTION

The present invention broadly contemplates the provision of aqueous solutions of amino acids wherein the amino acid content consists essentially of essential and non-essential L-amino acids in proportions or concentrations for achieving and maintaining (in a patient to whom the solution is parenterally administered, i.e., at an appropriate rate) a plasma amino acid pattern within established or predetermined ranges for a desired postprandial plasma amino acid pattern. The invention, in this broad sense, embraces such solutions, methods of formulating such solutions, and methods of treating patients by parenteral administration of such solutions. For administration to infants, the normal plasma amino acid pattern used is the post-prandial pattern for a normal infant on a normal feeding schedule. It is at present preferred, in such case, to use the two-hour post-prandial pattern of the breast-fed normal infant.

As used herein, the term "plasma amino acid pattern" refers to the absolute levels of essential and non-essential L-amino acids in the human plasma, and also to the molar ratios of total essential amino acids (TEAA) to total amino acids (TAA) and of each individual essential amino acid (EAA) to TEAA in the plasma, i.e., at any given point in time at which the same are measured. Established ranges for the normal infant two-hour postprandial plasma amino acid pattern, as have heretofore been determined, are set forth in the detailed description below.

In reviewing published data on the amino acid patterns of the post-prandial plasma of normal, growing infants fed a variety of nutritionally adequate formulas, applicants have discovered certain relationships to which reference may be made for assistance in understanding the invention. Specifically, in normal infants, after feeding, the concentration of virtually every amino acid in the plasma rises, reaches a peak and then falls. In young infants being fed on a 4-hour schedule, the available data suggests a cyclic rise and fall in the plasma amino acid concentrations occurring after each feeding. Closer examination of the available relevant post-prandial data reveals a set of definite but heretofore unrecognized interrelationships between the various amino acids. These are summarized as follows:

(1) The total molar concentration of all essential amino acids (TEAA), defined herein (for purposes of the present invention) as the 8 essential amino acids required by adults, viz. isoleucine (ILE), leucine (LEU), lysine (LYS), methionine (METE), phenylalanine (PHE), threonine (THR), tryptophan (TRY) and valine (VAL), plus histidine (HIS), tyrosine (TYR) and cysteine (CYS)—known to be required by infants—rises about 40% over the fasting level, in cow's milk-based formula feeding.

(2) The total molar concentration of all amino acids (TAA) also rises by about 40%, in cow's milk-based formla feeding.

(3) Hence the molar ratio of TEAA/TAA remains nearly constant, at a value of about 0.40, in the post-prandial plasma.

(4) The molar concentration of each individual essential amino acid (EAA) rises after feeding, but in an apparently fixed relationship to the rise in TEAA so that the individual EAA/TEAA ratios in post-prandial plasma are remarkably similar to those observed in the fasting state. Actually, in young infants being fed at frequent intervals, it is likely that a true fasting level is not reached after the post-prandial peak; rather the fall following the peak comes to rest at some point between the peak post-prandial level and the "true" fasting level.

(5) In surveying the effects of the quality of the protein intake (i.e., its specific amino acid composition) on the above interrelationships in the post-prandial plasma, applicants have noted that the plasma TEAA/TAA as well as the plasma individual EAA/TEAA for the various EAA show differences from the corresponding ratios in the dietary protein sources (human milk protein, cow's milk protein, fortified soy bean plasma protein, complete pure amino acid mixture, and casein hydrolysate). However, the plasma TEAA/TAA and the plasma individual EAA/TEAA show a constancy that is largely independent of the enteral protein intake so long as the latter is completely adequate nutritionally. It should be noted that with dietary deficiencies of at least three different EAA—tyrosine, methionine and lysine—the corresponding post-prandial plasma ratios for each (i.e., TYR/TEAA, MET/TEAA, and LYS/TEAA) have proven to be more sensitive indicators of deficiency than are the absolute plasma levels of these deficient amino acids.

Since the ratio of TEAA/TAA and individual EAA/TEAA of the diet show major differences from those observed in the post-prandial plasma, it is apparent that a considerable degree of regulation is being exerted by the liver and the gastrointestinal tract. This regulation seems to be directed in such a manner as to cause a rearrangement of the dietary amino acids such as to produce the characteristic ratios and interrelationships seen in the post-prandial plasma.

(6) The remarkable constancy of the post-prandial amino acid pattern, as defined above, in turn closely resembles estimates of the amino acid composition of new body protein which is deposited by the human infant over the first six months of life, as well as of the protein laid down by the growing fetus over the last part of pregnancy. Thus, it appears that the plasma post-prandial TEAA/TAA and individual EAA/TEAA ratios are in a sense precursors of new tissue protein which is the sine qua non of anabolism.

(7) A further argument in favor of assigning biological significance to the post-prandial pattern of the plasma amino acids derives from experiments in rats in which net tissue protein synthesis occurred in a close temporal relationship to feeding. In these experiments, after a single feeding, protein synthesis was accelerated, reached a peak and then declined to baseline, only to rise again if another feeding was taken, but falling below baseline if the next feeding was omitted.

The novel theoretical basis of this invention is the realization that the post-prandial plasma of normal infants provides the best and most physiologically based set of end-points to be achieved during parenteral nutrition. Given this, the invention embraces a noval amino acid mixture whose composition is such that all of these end-points will be achieved during parenteral nutrition. The theoretical basis of this solution thus differs markedly from all other amino acid solutions that are available, in that such solutions have generally been based either on more or less faithful copies of the amino acid compositions of high quality dietary proteins or on some variation of the known, essential amino acid requirements for oral nutrition of infants or adults as supplemented and modified by postulated theoretical, but largely untested assumptions concerning the needs for non-essential amino acids when given by the parenteral route.

It should be emphasized that the amino acid solution of the present invention is not in itself a direct copy of the post-prandial pattern. This is a very important point since it has sometimes been assumed that in parenteral nutrition, the resulting plasma amino acid patterns reflect the composition of the infusate. On the basis of applicants' own extensive work, this postulate has now been shown to be invalid. Whereas it is true that each of the presently available amino acid solutions produces a characteristic plasma pattern, that pattern, especially when it is expressed in terms of the plasma TEAA/TAA and the individual EAA/TEAA ratios, is markedly different from the corresponding ratios in the infusate. Thus, even when the liver and the gastrointestinal tract are largely bypassed, as in the case with parenteral nutrition, there are many physiological processes at work (anabolism, catabolism, metabolic transformation and renal excretion among others) which summate to yield the characteristic pattern typical of the particular amino acid solution being infused.

More particularly, a significant reason for the provision of an amino acid solution, for parenteral nutrition, having a composition that achieves and maintains (in an infant to whom it is administered) a steady-state plasma amino acid pattern within established ranges for the normal infant two-hour post-prandial amino acid pattern is that in normal infants, the post-prandial rise in plasma amino acid concentrations reaches a peak assumed to be two hours after a feeding. Thus, if the infant is fed every four hours, all tissues, including the developing nervous system, are exposed to this peak six times each day. This peak value may therefore be regarded as a safe and biologically acceptable value. Protein synthesis is thought to be related to this cyclic pattern of the plasma amino acid concentration with anabolism occurring post-prandially and catabolism pre-prandially.

Evidence for this hypothesis is the rise in the RNA/DNA ratio following a feeding. These considerations indicate that the two hour post-prandial values are the levels to achieve for optimal growth. In other words, then, defining the goal as the normal infant two-hour post-prandial plasma amino acid pattern is likely to be both safe, since it is the pattern found in normal infants fed formula orally, and effective for growth, since current concepts of growth suggest that the post-prandial rise in amino acid levels accelerates growth. Thereby, there may be provided an amino acid composition of a solution for intravenous infusion, which when combined with sufficient calories, will sustain a steady growth rate and will be likely to produce a normal plasma amino acid concentration.

Specifically, the present invention contemplates the provision of aqueous amino acid solutions for parenteral administration having in preferred embodiments an amino acid content consisting essentially of the essential and non-essential L-amino acids set forth below, in the following ranges of proportions or concentrations (expressed both as mM/dl and grams per liter). In this and all subsequent tables the ranges listed were calculated on the basis of a 5% solution (TAA=5 g/dl) and all concentrations herein expressed are to be understood as normalized to a 5% solution, except where expressly indicated to the contrary.

TABLE 1

| Amino Acids | mM/dl | g/l |
|---|---|---|
| essential | | |
| L-threonine | 1.03-3.30 | 1.23-3.93 |
| L-valine | 3.03-4.13 | 3.54-4.83 |
| L-leucine | 3.62-10.63 | 4.74-13.92 |
| L-isoleucine | 1.76-4.12 | 2.31-5.40 |
| L-lysine | 0.41-6.55 | 0.60-9.56 |
| L-methionine | 0.55-1.66 | 0.82-2.47 |
| L-cysteine | 0-3.00 | 0-3.63 |
| L-histidine | 0.43-5.48 | 0.67-8.49 |
| L-phenylalanine | 1.07-2.09 | 1.76-3.45 |
| L-tyrosine | 0-1.32 | 0-2.39 |
| L-tryptophan | 0.20-0.98 | 0.41-2.00 |
| nonessential | | |
| L-arginine | 1.46-6.76 | 2.54-11.76 |
| L-serine | 0.81-2.71 | 0.85-2.75 |
| L-proline | 106-4.42 | 1.22-5.08 |
| glycine | 1.92-4.44 | 1.44-3.33 |
| L-alanine | 1.30-4.66 | 1.16-4.15 |
| L-aspartic acid | 0-2.40 | 0-3.19 |
| L-glutamic acid | 0.31-2.55 | 0.46-3.75 |

The invention further contemplates the specific provision of certain especially preferred solutions, within the foregoing ranges.

The concentrations listed in Table 1 are for the purpose of illustrating preferred aqueous amino acid solutions according to the present invention. It should be understood that different concentrations may be used provided that they are pharmaceutically acceptable and nutritionally sufficient to provide to a patient. In other words, it is the relative proportions of amino acids to one another that forms the basis of the present invention and it should not be limited to any specific concentrations.

Additionally, the invention contemplates the provision of a method of supplying amino acids to a patient for promoting growth of lean body mass, comprising parenterally administering to the patient an aqueous L-amino acid solution having an amino acid content consisting essentially of essential and non-essential amino acids in proportions for achieving and maintaining, in an infant to whom the same is administered, a steady-state plasma amino acid pattern within established ranges for the normal infant two-hour post-prandial plasma amino acid pattern. The patient may be an infant, or (within the broad scope of the method of the invention) an older child or adult in need of repletion of lean body mass. In this connection, it may be explained that although the formulation of the solutions of the invention is directly predicated on considerations relating to growth of the human infant receiving TPN, and although the foregoing method is defined with reference thereto, it is believed that they are also applicable to the problem of "regrowth" of the depleted adult. A prior, a broad area of metabolic commonality between the processes of growth and "regrowth" would be expected and there have been some animal studies that can be interpreted as supporting this belief, indicating the conclusion that the particular amino acid solution which produces optimal anabolism in the growing infant will also produce optimal "regrowth" of the depleted adult.

Additionally, the invention embraces a method of preparing an amino acid solution for parenteral administration capable of producing and maintaining in an infant to whom the same in administered, a steady state plasma amino acid pattern within established ranges for the normal infant two-hour post-prandial plasma amino acid pattern. This method broadly comprises parenterally administering, to a plurality of infants, a plurality of different aqueous solutions each containing known proportions of essential and non-essential L-amino acids, to establish in each instance a steady-state plasma amino acid pattern; ascertaining each steady-state plasma amino acid pattern thus established; deriving from the ascertained patterns and the known proportion of amino acids in the administered solutions a series of relationships between the proportions of amino acids in administered solutions and the steady-state plasma amino acid pattern produced by parenteral administration of the solutions to infants; determining, from these relationships and the established ranges for the normal infant two-hour post-prandial plasma amino acid patterns, proportions of essential and non-essential amino acids which, in combination in an aqueous solution parenterally administered to an infant, produce in the infant a steady-state plasma amino acid pattern within the last-mentioned established ranges; and preparing an aqueous amino acid solution having an amino acid content consisting essentially of essential and non-essential L-amino acids in the proportions thus determined.

Further in accordance with the invention, in this method of preparation, each steady-state plasma amino acid pattern is ascertained by measuring the molar level of each essential and non-essential amino acid of a predetermined group present in the plasma, and combining the measurements thus made to ascertain the molar level of total essential amino acids of the group present in the plasma, the molar level of total amino acids of the group present in the plasma, the molar ratio of total essential amino acids to total amino acids of the group present in the plasma, and the molar ratio of each essential amino acid of the group to total essential amino acids of the group present in the plasma; the aforesaid relationships are then derived from the values of the aforesaid molar ratios and the molar levels of the non-essential amino acids of the group present in the plasma, and from the known proportions of amino acids in the group present in the administered solutions.

Further features and advantages of the invention will be apparent from the detailed description hereinbelow set forth.

DETAILED DESCRIPTION

Solutions embodying the invention were developed through an approach involving two steps. First, a number of different amino acid solutions were studied in infants requiring parenteral nutrition. For each solution, a number of steady-state plasma amino acid determinations were carried out. In all, seven different solutions were studied and a total of nearly 250 data points were accumulated, each data point representing a complete plasma aminogram. Since each solution has a known and unique composition it was possible to ascertain the effects of varying intake of each amino acid present in each of the various solutions upon the steady-state plasma concentrations of that particular amino acid. Such relationships are analagous to the dose (intake) versus response (plasma concentrations) curves of classical pharmacology. These relationships were determined for all amino acids except tyrosine and cysteine, which, because of their sparse solubility, are not present to any appreciable extent in any presently available solutions. These two amino acids were handled in a different way.

The second step in the development process concerned the mathematical treatment of the above data to detect interactions in the intake of the various amino acids on the plasma level of each amino acid. To take a specific example, the first step (above) could be depicted by ascertaining the effects of varying the intake of amino acid A on the steady-state plasma level of A. The second step then examined the data for possible interactions of the intake of amino acids B, C, D, E, etc., on the plasma level of A.

Having completed steps 1 and 2, it was then possible to designate specific goals;

(1) the absolute post-prandial plasma concentration for each of the amino acids, and (2) post-prandial plasma individual EAA/TEAA ratios and the post-prandial plasma TEAA/TAA ratio. By specifying these post-prandial goals the corresponding intakes needed to meet such goals were determined.

The specific goals of normal infant two-hour post-prandial plasma levels of each of the amino acids and the calculated molar ratios of individual EAA/TEAA and TEAA/TAA have been established as the mean±two standard deviations derived from the data for which the mean and outside ranges are shown in Table 2.

TABLE 2

| Amino Acid | Two-Hour Post-Prandial Plasma Target Ranges | |
|---|---|---|
| | Outside Range | Mean |
| | Concentration (μ mole/dl) | |
| Isoleucine | 2.8–8.8 | 5.8 |
| Leucine | 5.7–16.6 | 11.1 |
| Lysine | 8.4–22.7 | 15.6 |
| Methionine | 1.4–4.9 | 3.2 |
| Phenylalanine | 2.3–6.8 | 4.6 |
| Tryptophan | 2.0–9.8 | 5.9 |
| Threonine | 7.4–19.3 | 13.3 |
| Valine | 9.3–21.8 | 15.5 |
| Tyrosine | 4.5–13.3 | 8.9 |
| Cysteine | 3.6–6.8 | 5.2 |
| Histidine | 3.6–11.6 | 7.6 |
| Arginine | 4.6–14.5 | 9.5 |
| Alanine | 14.1–63.1 | 38.6 |

TABLE 2-continued

| Amino Acid | Two-Hour Post-Prandial Plasma Target Ranges | |
|---|---|---|
| | Outside Range | Mean |
| Proline | 9.0–31.2 | 20.1 |
| Glycine | 8.6–36.7 | 22.6 |
| Serine | 7.6–20.9 | 14.3 |
| Glutamic Acid | 3.1–23.6 | 13.4 |
| Aspartic Acid | 0.6–4.9 | 2.8 |
| | Molar Ratios | |
| ILE/TEAA (isoleucine) | 0.045–0.078 | 0.060 |
| LEU/TEAA (leucine) | 0.085–0.144 | 0.114 |
| LYS/TEAA (lysine) | 0.133–0.187 | 0.160 |
| MET/TEAA (methionine) | 0.017–0.048 | 0.033 |
| PHE/TEAA (phenylalanine) | 0.034–0.060 | 0.047 |
| TRY/TEAA (tryptophan) | 0.035–0.086 | 0.061 |
| THR/TEAA (threonine) | 0.096–0.180 | 0.138 |
| VAL/TEAA (valine) | 0.132–0.189 | 0.161 |
| TRY-TEAA (tyrosine) | 0.043–0.144 | 0.093 |
| CYS/TEAA (cysteine) | 0.036–0.073 | 0.055 |
| HIS/TEAA (histidine) | 0.056–0.102 | 0.079 |
| TEAA/TAA | 0.286–0.432 | 0.444 |

Table 2 thus defines the aforementioned established ranges for the normal infant two-hour post-prandial amino acid pattern.

The amino acid solution derived from the approach herein described is designed to affect the steady-state plasma amino acid concentrations during TPN in infants, children and adults in the following manner: (1) Maintain the absolute concentration of all amino acids, both essential and non-essential, in the plasma in the previously defined normal post-prandial ranges. (2) Maintain the plasma molar TEAA/TAA ratio as well as the individual EAA/TEAA ratios in the previously defined normal post-prandial ranges for patients of all ages; in the former case, the EAA consists of the 8 amino acids needed for enteral nutrition by adults (valine, isoleucine, leucine, methionine, lysine, phenylalanine, tryptophan and threonine), plus histidine, cysteine and tyrosine. In adults, these are probably also essential during parenteral nutrition, although they may not be essential in enteral nutrition. These considerations are secondary to the objective of normalizing plasma concentrations, both in absolute terms and in terms of their ratios of HIS/TEAA, CYS/TEAA and TYR/TEAA.

In a preferred embodiment of the invention the solution contains L-essential and non-essential amino acids and/or their metabolic precursors in a novel mixture, which, upon parenteral administration, will result in both plasma amino acid concentrations and the molar ratios being within normal ranges. The solution preferably contains 25 to 10 percent weight/volume of L-amino acids and/or biological equivalents, and necessary antioxidants, acids and/or bases suitable for pH adjustments.

Solutions embodying the invention, may also include other amino acids, e.g., asparagine or glutamine, or other nitrogen-containing compounds such as ornithine or taurine.

Table 3 compares a solution embodying the invention to the amino acid content of hen's egg proteins, one of nature's most efficiently utilized protein sources, and to other amino acid formulations for parenteral administration. As compared to the protein, the solution of the invention (PN V) has an unusually high percentage of branched chain amino acids (30 vs. 22%), total essential amino acids (55 vs. 45%), and the high essential amino acids to total nitrogen ratio (3.5 vs. 3.2). On the other hand, total sulfur, and tryptophan are exceptionally low.

TABLE 3
CALCULATED PARAMETERS OF AMINO ACID MIXTURES

|  | Hen's Egg | PN I | PN II | PN III | PN IV | PN V |
|---|---|---|---|---|---|---|
| A/E, mg/g | | | | | | |
| Isoleucine | 148 | 150 | 153 | 122 | 178 | 149 |
| Leucine | 197 | 195 | 200 | 158 | 356 | 254 |
| Lysine | 143 | 157 | 153 | 147 | 107 | 149 |
| Methionine | 69 | 114 | 85 | 147 | 13 | 62 |
| Total Sulfur AA | 107 | 117 | 85 | 147 | 99 | 65 |
| Phenylalanine | 130 | 121 | 94 | 157 | 89 | 87 |
| Total Aromatic AA | 195 | 121 | 105 | 166 | 100 | 100 |
| Tryptophan | 36 | 33 | 34 | 46 | 27 | 36 |
| Threonine | 114 | 86 | 111 | 107 | 53 | 76 |
| Valine | 163 | 142 | 170 | 118 | 178 | 141 |
| Essential AA, % w/w | 45 | 48 | 48 | 39 | 59 | 55 |
| BCAA, % w/w | 22 | 23 | 25 | 16 | 42 | 30 |
| Total Nitrogen, % w/w | 13.6 | 15.7 | 15.9 | 16.8 | 15.4 | 15.5 |
| E/T | 3.2 | 3.0 | 3.0 | 2.3 | 3.8 | 3.5 |
| EAA/TEAA Molar Ratios | | | | | | |
| ILE/TEAA | 0.129 | 0.148 | 0.148 | 0.117 | 0.160 | 0.144 |
| LEU/TEAA | 0.173 | 0.193 | 0.193 | 0.152 | 0.319 | 0.245 |
| LYS/TEAA | 0.113 | 0.139 | 0.133 | 0.128 | 0.086 | 0.129 |
| MET/TEAA | 0.054 | 0.099 | 0.072 | 0.125 | 0.010 | 0.052 |
| PHE/TEAA | 0.090 | 0.095 | 0.072 | 0.121 | 0.063 | 0.067 |
| TRY/TEAA | 0.020 | 0.021 | 0.021 | 0.028 | 0.015 | 0.022 |
| THR/TEAA | 0.110 | 0.094 | 0.118 | 0.113 | 0.053 | 0.081 |
| VAL/TEAA | 0.160 | 0.157 | 0.184 | 0.126 | 0.179 | 0.152 |
| TYR/TEAA | 0.060 | 0 | 0.006 | 0.007 | 0.007 | 0.030 |
| CYS/TEAA | 0.051 | 0.003 | 0 | 0 | 0.073 | 0.004 |
| HIS/TEAA | 0.040 | 0.051 | 0.052 | 0.091 | 0.034 | 0.071 |
| TEAA/TAA Molar Ratio | 0.481 | 0.431 | 0.433 | 0.339 | 0.636 | 0.567 |

In Table 3, PN V is a solution embodying the invention. PN I, II and III are commercially available amino acid solutions for parenteral nutrition, respectively identified by the trade names "FreAmine III," "Aminosyn," and "Travasol." PN IV is a formulation in accordance with U.S. Pat. No. 3,832,465 for parenteral nutrition. A/E is the weight ratio of the specific acid(s) to total essential amino acids ("Essential AA"); BCAA is branched chain amino acids; and E/T is the aforementioned ratio of essential amino acids to total nitrogen.

When the solution of the invention (PN V) is compared to the formulation described in U.S. Pat. No. 3,832,465 (PN IV in Table 3) surprising differences required for meeting the objective of normal post-prandial amino acid concentrations are the higher content of methionine (as reflected in A/E values, 62 vs. 13), threonine (76 vs. 53) and total tyrosine (expressed as its molar ratio TYR/TEEA, 0.030 vs. 0.007). On the other hand, lower leucine (A/E, 254 vs. 356) and cysteine (molar ratios, 0.004 vs. 0.073) are required for the use of this invention.

A solution of the invention, as exemplified by the foregoing, has the following characteristics which differentiate it clearly from all other amino acid solutions that are currently used for the purposes of promoting growth in infants or regrowth in adults receiving parenteral nutrition:

(1) The TEAA/TAA ratio of the solution ranges from 0.50 to 0.70, values which are very much higher than any commercially available solutions.

(2) The individual EAA are present in amounts to provide at least the estimated oral requirements for each EAA for both infants and adults when administered in doses of 2.0–3.5 g/kg/day and 1.0–2.5 g/kg/day, respectively.

(3) The solution contains a high content of the three branched chain amino acids, valine, leucine and isoleucine.

(4) The solution contains up to 7% (w/w/) of L-methionine and 11/3% (w/w) of L-phenylalanine, amounts which are likely to result in conversion of these two amino acids to cysteine and tyrosine, respectively, if the enzymatic pathways for such conversions are intact, and which did not exceed the upper limits of the post-prandial ranges in young infants.

(5) The solution contains up to 650 mg/l of L-tyrosine, which is the practical achievable maximal amount considering the sparse solubility of this amino acid.

(6) The solution contains up to 12.5% (w/w) of N-Acetyl-L-Tyrosine, a soluble metabolizable derivative of tyrosine; only by the addition of this compound can the plasma tyrosine concentration be normalized to the post-prandial range.

(7) The non-essential amino acids comprise about 30–50% of the total amino acids of the solution.

(8) The arginine content of the solution is sufficiently high to prevent arginine-responsive hyperammonemia at the usual total amino acid dose of 1.5–3.5 g/kg/day for infants and 1.0–2.5 g/kg/day for adults.

(9) Because of the dimerization of L-cysteine leading to precipitation of L-cysteine, the present invention includes supplementation with L-cysteine.HCl as an additive just prior to use or a cysteine/cysteine precursor such as cysteine mono- and dipeptides, N-acetyl-L-cysteine or other cystine/cysteine derivatives.

The amino acids used in practicing the present invention are preferably pure amino acids. In general, the amino acids should be in their L-form, rather than D-form or a mixture of D and L. Also, in general, the amino acids are employed as free amino acids but can be as amino acid salts or derivatives. For example, L-lysine acetate may be used and derivatives of L-tyrosine which are converted to tyrosine in the body may also be used. Other examples include the keto acid analogs, depeptides, tripeptides and N-acetyl derivatives of the various amino acids. In addition, it is convenient to incorporate cysteine in the form of its hydrochloride salt (L-cysteine HCl.H₂O). Reference herein to amino acids, in descriptions of specific compositions in accordance with the invention, will be understood to include such acids present as such salts or derivatives (except where the salt or derivative is expressly mentioned) and proportions or concentrations in such case will be understood to indicate the free amino acid equivalent of the salt or derivative.

It is understood that in addition to the nutritional ingredients, i.e., amino acids, electrolytes and vitamins, the formulation may include preservatives or stabilizers as required such as sodium bisulfite, ascorbic acid (vitamin C), or other compatible preservative agents. Nitrogen gas may also be used to preserve the solution.

The formulations are desirably free of ammonia. When prepared from crystalline amino acids, the resultant formulation will be low in free ammonia. In general, the formulations preferably contain less than 0.02% free ammonia.

The formulations may be advantageously prepared in the form of sterile aqueous solutions adapted for intravenous administration. In accordance with known practices for preparing such solutions, the solutions will be sterile, pyrogen-free, and have a suitable pH for intravenous administration. The most desirable pH for the solution may vary, but, in general, the pH of the solution can range from 5.0 to 7.8. In most cases where no nutrients are taken orally, the solutions described herein can be administered into a central vein which is a procedure known clinically as hyperalimentation. In this technique, either a subclavian or internal jugular indwelling catheter may be used.

Solutions prepared for intravenous administration can contain from 2.5 to 10 weight/volume (w/v) total amino acids. In preferred embodiments, which can be used for total parenteral nutrition, it is believed that the optimum concentrations of total amino acids will be from 4.0 to 7.0 weight/volume (w/v) percent as prepared for pediatric patients, 5.0 to 8.5 weight/volume (w/v) percent for mildly depleted adult patients who require hyperalimentation, and 8.5 to 10.0 weight/volume (w/v) for hyperalimentation of hypercatabolic, severely depleted adult patients. These concentrations are exemplary of commercial preparations prior to dilution for administration.

The solutions prepared as described above, when mixed with appropriate nutrients, are expected to provide full protein nutrition by administration of amounts supplying 2-5 grams total amino acids per kilogram of body weight, for pediatric patients. The maximum amount which may be administered will depend on the amino acid tolerance of the particular patient. The desirable clinical procedure may be to begin the infusion at a level below full protein nutriture, and gradually to increase the amount administered. For example, the administration to adult patients can be started at levels equivalent to about 20 to 25 grams of protein per day (24 hrs.), and then increased to at least 40 to 50 equivalent grams of protein per day. It is expected that the average patient will be able to tolerate at least the equivalent of 50 grams of protein per 24 hours, and in some cases, much higher administration levels up to as high as 100 to 140 grams protein equivalents may be feasible.

As will be understood, after parenteral administration of the amino acid solution reaches a steady state, a steady-state plasma amino acid pattern is achieved and maintained in the patient, in contrast to the cyclical or fluctuating pattern in a normal, orally fed individual. The compositions of the invention are intended, when administered to an infant on a steady-state basis in a TPN regimen, to enable attainment and maintenance of such a steady-state plasma amino acid pattern which is within the established ranges for the normal infant two-hour post-prandial pattern, including both absolute levels of amino acids and EAA/TEAA and TEAA/TAA molar ratios.

The amino acid contents of a series of specific amino acid solutions ("A," "B," and "C") embodying the invention, all embraced within the broad prefered composition ranges of Table 1 above, are set forth in Table 4 (in mM/dl) and Table 5 (in grams per liter). The ranges given in Tables 4 and 5 were determined by obtaining a value for each amino acid, in accordance with the formulation method of the invention, and taking as limits ±two standard deviations (S.D.) from that value. The "overall range" in Table 4 is the broad preferred range of Table 1. Composition C, in Tables 4 and 5, represents a currently especially preferred specific embodiment of the invention. It will be understood that each value in mM/dl, in Table 4, corresponds to the like value in g/l, in Table 5, for the same amino acid in the same solution A, B or C.

TABLE 4

| | Overall Range (ranges in mM/dl) | | Solution A | | Solution B | | Solution C | |
|---|---|---|---|---|---|---|---|---|
| | −2 S.D. | +2 S.D. | −2 S.D. | +2 S.D. | −2 S.D. | +2 S.D. | −2 S.D. | +2 S.D. |
| L-threonine | 1.03 | 3.30 | 1.03 | 1.69 | 2.02 | 3.30 | 1.34 | 2.19 |
| L-valine | 3.03 | 4.13 | 3.45 | 4.13 | 3.17 | 3.79 | 3.03 | 3.61 |
| L-leucine | 3.62 | 10.63 | 5.47 | 10.63 | 4.17 | 8.09 | 3.62 | 7.04 |
| L-isoleucine | 1.76 | 4.12 | 1.76 | 3.42 | 1.83 | 3.55 | 2.12 | 4.12 |
| L-lysine | 0.41 | 6.55 | 1.07 | 6.55 | 0.41 | 2.51 | 0.78 | 4.82 |
| L-methionine | 0.55 | 1.66 | 0.58 | 1.58 | 0.55 | 1.49 | 0.62 | 1.66 |
| L-cysteine | 0 | 3.00 | 0 | 3.00 | 0 | 3.00 | 0 | 3.00 |
| L-histidine | 0.43 | 5.48 | 0.43 | 1.85 | 1.28 | 5.48 | 0.59 | 2.63 |
| L-phenylalanine | 1.07 | 2.09 | 1.10 | 1.88 | 1.23 | 2.09 | 1.07 | 1.83 |
| L-tyrosine | 0.00 | 1.32 | 0 | 0.44 | 0.35 | 0.75 | 0.33 | 1.32 |
| L-tryptophan | 0.20 | 0.98 | 0.20 | 0.80 | 0.20 | 0.80 | 0.25 | 0.98 |
| TEAA | 12.10 | 43.26 | 15.09 | 35.93 | 15.21 | 34.85 | 13.75 | 33.20 |
| L-arginine | 1.46 | 6.76 | 1.46 | 4.36 | 2.26 | 6.76 | 1.75 | 5.25 |
| L-serine | 0.81 | 2.71 | 0.88 | 2.62 | 0.81 | 2.43 | 0.91 | 2.71 |
| L-proline | 1.06 | 4.42 | 1.12 | 3.38 | 1.06 | 3.18 | 1.48 | 4.42 |
| glycine | 1.92 | 4.44 | 2.96 | 4.44 | 2.46 | 3.70 | 1.92 | 2.88 |
| L-alanine | 1.30 | 4.66 | 1.56 | 4.66 | 1.30 | 3.90 | 1.50 | 4.50 |
| L-aspartic acid | 0 | 2.40 | 0 | 1.36 | 0 | 1.20 | 0 | 2.40 |
| L-glutamic acid | 0.31 | 2.55 | 0.37 | 1.11 | 0.31 | 0.93 | 0.85 | 0.55 |
| TNAA | 6.86 | 27.94 | 8.35 | 21.93 | 8.20 | 22.10 | 8.31 | 24.71 |
| TAA | 18.96 | 71.20 | 23.44 | 57.86 | 23.41 | 56.95 | 22.06 | 57.91 |
| TEAA/TAA | 0.63 | 0.61 | 0.64 | 0.62 | 0.65 | 0.61 | 0.62 | 0.57 |

TABLE 5

| | (g/l) | | | | | |
|---|---|---|---|---|---|---|
| | Solution A | | Solution B | | Solution C | |
| | −2 S.D. | +2 S.D. | −2 S.D. | +2 S.D. | −2 S.D. | +2 S.D. |
| L-threonine | 1.23 | 2.01 | 2.40 | 3.93 | 1.59 | 2.61 |
| L-valine | 4.04 | 4.83 | 3.71 | 4.43 | 3.55 | 4.22 |
| L-leucine | 7.17 | 13.93 | 5.46 | 10.60 | 4.74 | 9.22 |
| L-isoleucine | 2.31 | 4.48 | 2.40 | 4.65 | 2.77 | 5.40 |
| L-lysine | 1.56 | 9.56 | 0.60 | 3.66 | 1.14 | 7.04 |
| L-methionine | 0.86 | 2.35 | 0.82 | 2.22 | 0.92 | 2.47 |
| L-cysteine | 0 | 3.63 | 0 | 3.36 | 0 | 3.63 |
| L-histidine | 0.64 | 2.76 | 1.91 | 8.17 | 0.91 | 4.08 |
| L-phenylalanine | 1.82 | 3.10 | 2.03 | 3.45 | 1.77 | 3.02 |
| L-tyrosine | 0 | 0.80 | 0.63 | 1.36 | 0.60 | 2.39 |
| L-tryptophan | 0.41 | 1.63 | 0.41 | 1.63 | 0.51 | 2.00 |
| TEAA | 20.04 | 49.08 | 20.37 | 47.73 | 18.50 | 46.08 |
| L-arginine | 2.54 | 7.59 | 3.93 | 11.76 | 3.04 | 9.14 |
| L-serine | 0.92 | 2.75 | 0.85 | 2.55 | 0.96 | 2.84 |
| L-proline | 1.29 | 3.89 | 1.22 | 3.66 | 1.70 | 5.08 |
| glycine | 2.22 | 3.33 | 1.84 | 2.78 | 1.44 | 2.16 |
| L-alanine | 1.39 | 4.15 | 1.16 | 3.47 | 1.34 | 4.00 |
| L-aspartic acid | 0 | 1.81 | 0 | 1.60 | 0 | 3.19 |

TABLE 5-continued

|  | (g/l) | | | | | |
|---|---|---|---|---|---|---|
|  | Solution A | | Solution B | | Solution C | |
|  | −2 S.D. | +2 S.D. | −2 S.D. | +2 S.D. | −2 S.D. | +2 S.D. |
| L-glutamic acid | 0 | 1.63 | 0.46 | 1.37 | 1.25 | 3.75 |
| TNAA | 8.90 | 25.15 | 9.46 | 27.19 | 9.73 | 30.16 |
| TAA | 28.94 | 74.23 | 29.83 | 74.92 | 28.23 | 76.24 |

In the composition of these tables, the value of TEAA/TAA may, for example, range from about 0.58 to about 0.65.

As indicated above, the preceding examples are illustrative of preferred embodiments of the present invention. However, the invention should not be limited to any specific concentrations. Rather the present invention is directed to relative proportions among the various amino acids which may be present in any overall concentrations provided that the solution is pharmaceutically acceptable and nutritionally sufficient for the purposes desired.

More specifically, the present invention embodies any concentration of formulation provided that the relative proportions among the amino acids is maintained. This may be illustrated by the conversion of the overall ranges set forth in Table 1 and Table 4 to a series of ranges independent of concentration in solution. Such an example might take into account the fact that in each of the preferred embodiments, the total of the mean values for each amino acid is approximately 40 mM/dl. Therefore, the ranges could be converted to ranges having 100 moles as the total of the means merely by dividing each value by 0.40. These values have been calculated and set forth in Table 6. They have also been converted to weight ranges in this table.

The above discussion does not mean that any solution embodying the present invention should necessarily contain 40 mM/dl or that when a similar conversion is made, the total moles of amino acids should equal 100. Rather, it is an indication of the arbitrary nature of specific concentrations and that the present invention more properly is directed to relative proportions of amino acids, otherwise known as an amino acid pattern for the entire solution.

TABLE 6

|  | Relative Mole Ranges | | Relative Gram Ranges | |
|---|---|---|---|---|
| L-threonine | 2.60 | 8.25 | 2.46 | 7.86 |
| L-valine | 7.58 | 10.32 | 7.10 | 9.68 |
| L-leucine | 9.05 | 26.58 | 9.50 | 27.90 |
| L-isoleucine | 4.40 | 10.30 | 4.62 | 10.80 |
| L-lysine | 1.02 | 16.40 | 1.70 | 27.02 |
| L-methionine | 1.38 | 4.15 | 1.64 | 4.96 |
| L-cysteine | 0 | 7.50 | 0 | 7.28 |
| L-histidine | 1.08 | 13.70 | 1.34 | 17.00 |
| L-phenylalanine | 2.68 | 5.22 | 3.54 | 6.90 |
| L-tyrosine | 0 | 3.30 | 0 | 4.78 |
| L-tryptophan | 0.50 | 2.45 | 0.82 | 4.00 |
| L-arginine | 3.65 | 16.90 | 5.08 | 23.56 |
| L-serine | 2.02 | 6.80 | 1.70 | 5.72 |
| L-proline | 2.65 | 11.05 | 2.44 | 10.18 |
| glycine | 4.80 | 11.10 | 2.88 | 6.66 |
| L-alanine | 3.25 | 11.65 | 2.32 | 8.30 |
| L-aspartic acid | 0 | 6.00 | 0 | 6.38 |
| L-glutamic acid | 0.78 | 6.38 | 0.90 | 7.50 |

As is readily apparent, the conversion of the relative mole ranges of Table 1 to those listed above by multiplying by a common factor of 0.40 has no effect on the relative amounts of total essential amino acids compared with the total amino acids. The same is true of the relative proportions of each of the amino acids as it relates to the others in the solution.

It is also contemplated that according to the present invention one may omit one or more of the non-essential amino acids while retaining the beneficial aspects of the present invention. That is, it is the amino acid pattern of the essential amino acids that is of primary importance and, as long as a sufficient amount of non-specific nitrogen is provided in the form of non-essential amino acids, the specific pattern of non-essential amino acids is not critical. Thus, a formula containing the amino acid pattern for the essential amino acids as described in Table 6 while varying or omitting entirely some of the non-essential amino acids, would still fall within the scope of the present invention.

By way of further illustration of the invention, reference may be made to the following specific examples:

EXAMPLE I

A series of sterile, non-pyrogenic, stable solutions (D, E and F) suitable for parenteral nutrition regimens were prepared from the amino acids set forth in Table 7, at concentrations (in grams per liter) falling within their specified ranges, with antioxidant and water in the concentrations also set forth in Table 7, the values of which are not normalized to a 5% solution as they are intended to be illustrative of commercial concentration.

TABLE 7

|  | Solution D | Solution E | Solution F |
|---|---|---|---|
| L-Isoleucine | 2.76–4.83 | 3.45–5.87 | 5.87–6.90 |
| L-Leucine | 7.60–13.30 | 9.50–16.15 | 16.15–19.00 |
| L-Lysine | 3.84–6.72 | 4.80–8.16 | 8.16–9.60 |
| L-Methionine | 1.12–1.96 | 1.40–2.38 | 2.38–2.80 |
| L-Phenylalanine | 1.80–3.15 | 2.25–3.83 | 3.83–4.50 |
| L-Tryptophan | 0.50–0.88 | 0.70–1.19 | 1.19–1.40 |
| L-Valine | 3.44–6.02 | 4.30–7.31 | 7.31–8.60 |
| L-Arginine | 4.80–8.40 | 6.00–10.20 | 10.20–12.00 |
| L-Histidine | 1.36–2.38 | 1.70–2.89 | 2.89–3.40 |
| L-Threonine | 1.60–2.80 | 2.00–3.40 | 3.40–4.00 |
| L-Alanine | 2.08–3.64 | 2.60–4.42 | 4.42–5.20 |
| L-Proline | 3.04–5.32 | 3.80–6.46 | 6.46–7.60 |
| Glycine | 1.36–2.38 | 1.70–2.89 | 2.89–3.40 |
| L-Serine | 1.36–2.38 | 1.70–2.89 | 2.89–3.40 |
| L-Tyrosine | 0.0–0.65 | 0.0–0.65 | 0.0–0.65 |
| L-Glutamic Acid | 1.12–1.96 | 1.40–2.38 | 2.28–2.80 |
| L-Aspartic Acid | 0.40–0.70 | 0.50–0.85 | 0.85–1.00 |
| L-Cysteine.HCl.H$_2$O | 0.20 | 0.20 | 0.20 |
| N—Acetyl-L-Tyrosine | 2.00–3.50 | 2.50–4.25 | 4.25–5.00 |
| Potassium Metabisulfite | 0–0.55 | 0–0.55 | 0 0.55 |
| Phosphoric Acid 85% | 0–0.264 ml | 0–0.264 ml | 0–0.264 ml |
| Glacial Acetic Acid | pH Adjustment | pH Adjustment | pH Adjustment |
| Water for Injection | q.s. | q.s. | q.s. |

In the manufacture of the solutions described herein, the order of mixing of the potentially incompatible ingredients is crucial for the preparation of stable units. The acceptable order of mixing is, but not limited to, the following:

1. All amino acids except L-tryptophan and L-cysteine HCl H$_2$O
2. Phosphoric acid 85% reagent grade
3. Glacial acetic acid, reagent grade
4. L-Tryptophan
5. L-cysteine HCl.H$_2$O
6. Potassium metabisulfite, reagent grade 7. Water for injection, USP Solutions made by using this order of addition and composition can be packaged in standard intravenous containers and steam sterilized. Standard sterilization cycles and equipment can be used.

Solution D, having a TAA concentration within the approximate range of 4.0 to 7.0 weight percent, is suitable for parenteral nutrition of pediatric patients. Solution E, having a TAA concentration within the approximate range of 5.0 to 8.5 weight percent, is suitable for parenteral nutrition of mildly depleted adult patients. Solution F, having a TAA content within the approximate range of 8.5-10.0 weight percent, is suitable for parenteral nutrition of severely depleted adult patients.

EXAMPLE II

A method of preparing amino acid solutions in accordance with the invention is exemplified by the following procedures, which employed established values of the normal infant two-hour post-prandial plasma amino acid pattern and 161 separate determinations of plasma amino acids on 94 infants who received one of six different amino acid solutions. In this procedure, the essential amino acid data were expressed as ratios: the ratio of the total essential amino acids (TEAA) to total amino acids (TAA) and the ratios of the individual essential amino acid (IEAA) to TEAA. Essential amino acids were taken to include all the amino acids usually thought to be essential for the adult plus histidine, cystine and tyrosine which are thought to be essential for the prematurely born infant. Tryptophan, for which no data are available, was excluded. Since the plasma level of tryptophan is low relative to other amino acids, omission of tryptophan makes little difference to the calculated ratios.

The reasons for the ratio approach to analyzing plasma amino acid data may be summarized as follows:
1. while the absolute levels of amino acids rise postprandially the ratio of TEAA/TAA and the ratios of individual (ind.) EAA/TEAA remain quite constant;
2. while ind. EAA/TEAA ratios in the various intakes tested (cow's milk, casein hydrolysate, etc.) varied by more than 25%, the corresponding plasma ratios showed much less variation;
3. the estimated ind. EAA/TEAA ratios of the net protein gained by the human infant over the first six months of life are similar to the corresponding plasma ratios;
4. in examining the 161 plasma aminograms obtained in the present procedure, it is noted that there is a significant reduction in the coefficient of variation of the data for a fixed intake when the data are expressed as ratios rather than as absolute levels.

All patients were receiving lipid-free total parenteral nutrition delivering 2 to 3 gms/kg day of amino acids and were in a metabolic steady state, on full strength intake, exhibiting steady weight gain and positive nitrogen balance with no metabolic or septic complications. The patients were term infants studied in the first six months of life. Blood for amino acid analysis was collected in the morning in heparin, immediately spun and the plasma deproteinized with sulfosalicylic acid. The patients received one of six different intakes:

|  | number of data points (plasma aminograms) |
|---|---|
| "FreAmine" or "FreAmine II" (2.5 g/kg/d) | 61 |
| "Aminosyn" at 2.0, 2.5 or 3.0 g/kg/d | 54 |
| "NeoAminosol" (2.5 g/kg/d) | 7 |
| Cutter amino acid solution (2.5 g/kg/d) | 8 |
| Casein hydrolysate (3.0 g/kg/d) | 16 |
| Fibrin Hydrolysate (3.0 g/kg/d) | 15 |
|  | 161 |

All aminograms were treated as if they were independent since the within-patient variation was as large as the between-patient variation. The ratios were calculated and all data were subjected to a stepwise multiple regression analysis. The plasma ratio or level of each amino acid was the dependent variable and the ratio or level of all amino acids in the six intake solutions were the independent variables. All possible regressions were explored with variables added or deleted at the 5% level and the equation with the smallest residual error was selected. The intake ratio or level of an amino acid was forced in where the plasma ratio or level of that amino acid was the dependent variable. The multiple regression coefficient for these equations ranged from 0.49 to 0.88 (see Table 8) and, with an n of 161, all were significantly different from zero ($P<0.01$).

TABLE 8

MULTIPLE REGRESSION RESULTS

| PLASMA AMINO ACID | INTAKE AMINO ACID INCLUDED IN EQUATION | MULTPLE CORRELATION COEFFICIENT | MAXIMUM CORRELATION COEFFICIENT POSSIBLE |
|---|---|---|---|
| Threonine | threonine, leucine | 0.730 | 0.731 |
| Valine | valine, phenylalanine | 0.841 | 0.848 |
| Leucine | leucine, TEAA/TAA | 0.820 | 0.825 |
| Isoleucine | isoleucine, leucine, tyrosine, cystine | 0.534 | 0.535 |
| Lysine | lysine, tyrosine, cystine, threonine | 0.445 | 0.477 |
| Methionine | methionine, histidine, TEAA/TAA, isoleucine | 0.829 | 0.841 |
| Histidine | histidine, leucine, TEAA/TAA, isoleucine | 0.730 | 0.732 |
| Phenylalanine | phenylalanine, isoleucine | 0.790 | 0.793 |
| Tyrosine | tyrosine, threonine, lysine | 0.533 | 0.537 |
| Arginine | arginine, alanine | 0.586 | 0.613 |
| Serine | serine, proline, phenylalanine | 0.590 | 0.599 |
| Proline | proline, aspartic acid, glutamic acid | 0.647 | 0.670 |
| Glycine | glycine | 0.825 | 0.857 |
| Alanine | alanine, serine, methionine, aspartic acid | 0.733 | 0.733 |
| Aspartic Acid | aspartic acid, methionine, alanine | 0.536 | 0.550 |
| Glutamic Acid | glutamic acid, alanine, arginine | 0.736 | 0.738 |
| TEAA/TAA | TEAA/TAA, lysine | 0.875 | 0.878 |

The amino acid composition of the intake was computed by setting the dependent variable in each of the 15 equations to the corresponding normal infant two-hour post-prandial value and then solving all 15 equations simultaneously for the intake ratios or levels. This process was subject to several constraints:
1. intake level of cystine was set to zero due to solubility limitations and the corresponding equation deleted;
2. the intake level of tyrosine was set to 0.24 mM/dl due to solubility limitations, and the corresponding equation deleted;
3. arginine intake was set to 3.0 mM/dl, an amount previously found to prevent NH$_3$ accumulation;
4. tryptophan, which is not usually measured and for which data were not avilable, was included in the proposed solution at an arbitrary concentration of 0.40 mM/dl, a value not too dissimilar from other crystalline amino acid solutions;
5. all the nonessential amino acids, except arginine, were included using the multiple regression equations for concentration rather than the ratio equations.

The results of these computations are given in Table 9 and represent the amino acid composition of a solution in accordance with the invention (Solution "G") that is believed likely to promote growth of an infant at the same time producing a normal plasma amino acid pattern. Table 9 also compares solution G with various known amino acid formulations for parenteral nutrition.

This multiple regression approach to predicting a solution composition is superior to a single variable approach because it takes into account the interaction of all other amino acids in determining the plasma ratios.

TABLE 9

| | (mM/dl) | | | | |
|---|---|---|---|---|---|
| | Solution G | "Aminosyn" | "FreAmine II" | "Travasol" | Cutter |
| Threonine | 1.40 | 2.18 | 1.68 | 1.82 | 0.84 |
| Valine | 3.91 | 3.42 | 2.81 | 1.96 | 1.33 |
| Leucine | 8.30 | 3.59 | 3.46 | 2.36 | 1.68 |
| Isoleucine | 2.67 | 2.75 | 2.65 | 1.82 | 2.37 |
| Lysine | 3.93 | 2.47 | 2.50 | 1.58 | 2.88 |
| Methionine | 1.18 | 1.34 | 1.78 (D,L) | 1.94 | 1.81 |
| Histidine | 1.17 | 0.97 | 0.91 | 1.41 | −0.97 |
| Phenylalanine | 1.53 | 1.33 | 1.71 | 1.87 | 1.51 |
| Tyrosine | 0.24 | 0.24 | 0 | 0.11 | 0 |
| Tryptophan | 0.40 | 0.39 | 0.37 | 0.44 | 0.25 |
| TEAA | 24.73 | 18.68 | 17.87 | 15.31 | 13.64 |
| Arginine | 3.00 | 2.82 | 1.05 | 2.98 | 2.70 |
| Serine | 1.80 | 2.00 | 2.80 | 0 | 0 |
| Proline | 2.33 | 3.74 | 4.86 | 1.89 | 0.60 |
| Glycine | 3.83 | 8.53 | 13.33 | 13.82 | 28.27 |
| Alanine | 3.21 | 7.19 | 3.97 | 11.64 | 0 |
| Aspartic Acid | 0.70 | 0 | 0 | 0 | 1.88 |
| Glutamic Acid | 0.77 | 0 | 0 | 0 | 1.82 |
| TNAA | 15.64 | 24.28 | 26.01 | 30.33 | 35.27 |
| TEAA/TAA | 0.608 | 0.434 | 0.407 | 0.335 | 0.279 |

These multiple regression equations are solved simultaneously by inverting the 15×15 matrix of multiple regression coefficients (many of which are, of course, zero). Although linear equations were employed in this Example for what is probably a nonlinear situation, the use of linear equations serves as an approximation.

Once a new amino acid composition has been formulated, it can be tested to verify attainment, in steady-state administration, of a plasma amino acid pattern within the desired two-hour post-prandial plasma values. The solution can be given to a relatively few patients (e.g., 4–6), necessary data collected from them, and a new solution composition formulated by the above procedure. Repetition of this cycle of computation, formulation and testing several times can refine the definition of the desired composition.

In the foregoing procedure, in ascertaining each of the 161 steady-state plasma amino acid patterns (data points) involved, the molar level of each of a predetermined group of amino acids was measured. The members of this group were the acids listed in Table 8.

As will be apparent to those skilled in the art, the ranges of individual nonessential amino acids in the solutions of the invention may depart by as much as 50% or perhaps even more in the case of aspartic and glutamic acids, from the ranges herein set forth without substantially affecting the properties and effects of the solutions. Accordingly, the ranges herein specified and claimed are to be construed as embracing solutions exhibiting such departures.

Although the present invention has been described with reference to the two-hour post-prandial values for an infant, it is to be understood that other post-prandial values, for example, values at one, four, six, or more hours after eating, could be used. Moreover, the invention may also be employed to prepare solutions useful in treating premature infants or depleted adult patients formulated so as to normalize to suitable post-prandial values, defined either directly or by reference to tissue composition.

It is to be understood that the invention is not limited to the features and embodiments hereinabove specifically set forth, but may be carried out in other ways without departure from its spirit.

What is claimed is:

1. A method of supplying amino acids to a patient, comprising parenterally administering to said patient an aqueous amino acid solution having an amino acid content consisting essentially of

| 1.03–3.30 mM/dl | L-threonine |
|---|---|
| 3.03–4.13 mM/dl | L-valine |
| 3.62–10.63 mM/dl | L-leucine |
| 1.76–4.12 mM/dl | L-isoleucine |
| 0.41–6.55 mM/dl | L-lysine |
| 0.55–1.66 mM/dl | L-methionine |
| 0–3.00 mM/dl | L-cysteine |
| 0.43–5.48 mM/dl | L-histidine |
| 1.07–2.09 mM/dl | L-phenylalanine |
| 0–1.32 mM/dl | L-tyrosine |
| 0.20–0.98 mM/dl | L-tryptophan |
| 1.46–6.76 mM/dl | L-arginine |
| 0.81–2.71 mM/dl | L-serine |
| 1.06–4.42 mM/dl | L-proline |
| 1.92–4.44 mM/dl | glycine |
| 1.30–4.66 mM/dl | L-alanine |
| 0–2.40 mM/dl | L-aspartic acid |
| 0.31–2.55 mM/dl | L-glutamic acid. |

2. A method according to claim 1, wherein said amino acid content consists essentially of

| 1.34–2.19 | mM/dl | L-threonine |
|---|---|---|
| 3.03–3.61 | " | L-valine |
| 3.62–7.04 | " | L-leucine |
| 2.12–4.12 | " | L-isoleucine |
| 0.78–4.82 | " | L-lysine |
| 0.62–1.66 | " | L-methionine |
| 0–3.00 | " | L-cysteine |
| 0.59–2.63 | " | L-histidine |
| 1.07–1.83 | " | L-phenylalanine |

-continued

| | | |
|---|---|---|
| 0.33–1.32 | " | L-tyrosine |
| 0.25–0.98 | " | L-tryptophan |
| 1.75–5.25 | " | L-arginine |
| 0.91–2.71 | " | L-serine |
| 1.48–4.42 | " | L-proline |
| 1.92–2.88 | " | glycine |
| 1.50–4.50 | " | L-alanine |
| 0–2.40 | " | L-aspartic acid |
| 0.85–2.55 | " | L-glutamic acid. |

3. A method according to claim 1, wherein said amino acid content consists essentially of

| | | |
|---|---|---|
| 1.03–1.69 | mM/dl | L-threonine |
| 3.45–4.13 | " | L-valine |
| 5.47–10.63 | " | L-leucine |
| 1.76–3.42 | " | L-isoleucine |
| 1.07–6.55 | " | L-lysine |
| 0.58–1.58 | " | L-methionine |
| 0–3.00 | " | L-cysteine |
| 0.43–1.85 | " | L-histidine |
| 1.10–1.88 | " | L-phenylalanine |
| 0–0.44 | " | L-tyrosine |
| 0.20–0.80 | " | L-trypotophan |
| 1.46–4.36 | " | L-arginine |
| 0.88–2.62 | " | L-serine |
| 1.12–3.38 | " | L-proline |
| 2.96–4.44 | " | glycine |
| 1.56–4.66 | " | L-alanine |
| 0–1.36 | " | L-aspartic acid |
| 0.37–1.11 | " | L-glutamic acid. |

4. A method according to claim 1, wherein said amino acid content consists essentially of

| | | |
|---|---|---|
| 2.02–3.30 | mM/dl | L-threonine |
| 3.17–3.79 | " | L-valine |
| 4.17–8.09 | " | L-leucine |
| 1.83–3.55 | " | L-isoleucine |
| 0.41–2.51 | " | L-lysine |
| 0.55–1.49 | " | L-methionine |
| 0–3.00 | " | L-cysteine |
| 1.28–5.48 | " | L-histidine |
| 1.23–2.09 | " | L-phenylalanine |
| 0.35–0.75 | " | L-tyrosine |
| 0.20–0.80 | " | L-tryptophan |
| 2.26–6.76 | " | L-arginine |
| 0.81–2.43 | " | L-serine |
| 1.06–3.18 | " | L-proline |
| 2.46–3.70 | " | glycine |
| 1.30–3.90 | " | L-alanine |
| 0–1.20 | " | L-aspartic acid |
| 0.31–0.93 | " | L-glutamic acid. |

5. A method according to claim 1, wherein said solution has a molar ratio of total essential amino acids to total amino acids between about 0.58 and about 0.65.

6. A method of supplying amino acids to a patient, comprising parenterally administering to said patient an aqueous solution of essential and non-essential amino acids having an essential amino acid content consisting essentially of

| | | |
|---|---|---|
| 1.03–3.30 | mM/dl | L-threonine |
| 3.03–4.13 | " | L-valine |
| 3.62–10.63 | " | L-leucine |
| 1.76–4.12 | " | L-isoleucine |
| 0.41–6.55 | " | L-lysine |
| 0.55–1.66 | " | L-methionine |
| 0–3.00 | " | L-cysteine |
| 0.43–5.48 | " | L-histidine |
| 1.07–2.09 | " | L-phenylalanine |

-continued

| | | |
|---|---|---|
| 0–1.32 | " | L-tyrosine |
| 0.20–0.98 | " | L-tryptophan | and wherein said nonessential amino acids include one or more of the group consisting of L-arginine, L-serine, L-proline, glycine, L-alanine, L-aspartic acid, and L-glutamic acid.

7. An amino acid solution for parenteral nutrition comprising an aqueous solution of amino acids wherein the amino acid content consists essentially of

| | |
|---|---|
| 1.03–3.30 mM/dl | L-threonine |
| 3.03–4.13 mM/dl | L-valine |
| 3.62–10.63 mM/dl | L-leucine |
| 1.76–4.12 mM/dl | L-isoleucine |
| 0.41–6.55 mM/dl | L-lysine |
| 0.55–1.66 mM/dl | L-methionine |
| 0–3.00 mM/dl | L-cysteine |
| 0.43–5.48 mM/dl | L-histidine |
| 1.07–2.09 mM/dl | L-phenylalanine |
| 0–1.32 mM/dl | L-tyrosine |
| 0.20–0.98 mM/dl | L-tryptophan |
| 1.46–6.76 mM/dl | L-arginine |
| 0.81–2.71 mM/dl | L-serine |
| 1.06–4.42 mM/dl | L-proline |
| 1.92–4.44 mM/dl | glycine |
| 1.30–4.66 mM/dl | L-alanine |
| 0–2.40 mM/dl | L-aspartic acid |
| 0.31–2.55 mM/dl | L-glutamic acid. |

8. A solution as defined in claim 7, wherein said amino acid content consists essentially of

| | | |
|---|---|---|
| 1.34–2.19 | mM/dl | L-threonine |
| 3.03–3.61 | " | L-valine |
| 3.62–7.04 | " | L-leucine |
| 2.12–4.12 | " | L-isoleucine |
| 0.78–4.82 | " | L-lysine |
| 0.62–1.66 | " | L-methionine |
| 0–3.00 | " | L-cysteine |
| 0.59–2.63 | " | L-histidine |
| 1.07–1.83 | " | L-phenylalanine |
| 0.33–1.32 | " | L-tyrosine |
| 0.25–0.98 | " | L-tryptophan |
| 1.75–5.25 | " | L-arginine |
| 0.91–2.71 | " | L-serine |
| 1.48–4.42 | " | L-proline |
| 1.92–2.88 | " | glycine |
| 1.50–4.50 | " | L-alanine |
| 0–2.40 | " | L-aspartic acid |
| 0.85–2.55 | " | L-glutamic acid. |

9. A solution as defined in claim 7, wherein said amino acid content consists essentially of

| | | |
|---|---|---|
| 1.03–1.69 | mM/dl | L-threonine |
| 3.45–4.13 | " | L-valine |
| 5.47–10.63 | " | L-leucine |
| 1.76–3.42 | " | L-isoleucine |
| 1.07–6.55 | " | L-lysine |
| 0.58–1.58 | " | L-methionine |
| 0–3.00 | " | L-cysteine |
| 0.43–1.85 | " | L-histidine |
| 1.10–1.88 | " | L-phenylalanine |
| 0–0.44 | " | L-tyrosine |
| 0.20–0.80 | " | L-trypotophan |
| 1.46–4.36 | " | L-arginine |
| 0.88–2.62 | " | L-serine |
| 1.12–3.38 | " | L-proline |
| 2.96–4.44 | " | glycine |
| 1.56–4.66 | " | L-alanine |
| 0–1.36 | " | L-aspartic acid |

-continued

| | | |
|---|---|---|
| 0.37–1.11 | " | L-glutamic acid. |

10. A solution as defined in claim 7, wherein said amino acid content consists essentially of

| | | |
|---|---|---|
| 2.02–3.30 | mM/dl | L-threonine |
| 3.17–3.79 | " | L-valine |
| 4.17–8.09 | " | L-leucine |
| 1.83–3.55 | " | L-isoleucine |
| 0.41–2.51 | " | L-lysine |
| 0.55–1.49 | " | L-methionine |
| 0–3.00 | " | L-cysteine |
| 1.28–5.48 | " | L-histidine |
| 1.23–2.09 | " | L-phenylalanine |
| 0.35–0.75 | " | L-tyrosine |
| 0.20–0.80 | " | L-tryptophan |
| 2.26–6.76 | " | L-arginine |
| 0.81–2.43 | " | L-serine |
| 1.06–3.18 | " | L-proline |
| 2.46–3.70 | " | glycine |
| 1.30–3.90 | " | L-alanine |
| 0–1.20 | " | L-aspartic acid |
| 0.31–0.93 | " | L-glutamic acid. |

11. A solution as defined in claim 7, having a molar ratio of total essential amino acids to total amino acids between about 0.58 and about 0.65.

12. An amino acid solution for parenteral nutrition comprising an aqueous solution of amino acids having an amino acid content consisting essentially of essential and non-essential amino acids in proportions for producing and maintaining, in an infant to whom the same is administered, a steady-state plasma amino acid pattern within established ranges for the normal infant two-hour post-prandial plasma amino acid pattern, said content including the following amino acids in the following ranges:

| | | |
|---|---|---|
| 1.03–3.30 mM/dl | | L-threonine |
| 3.03–4.13 mM/dl | | L-valine |
| 3.62–10.63 mM/dl | | L-leucine |
| 1.76–4.12 mM/dl | | L-isoleucine |
| 0.41–6.55 mM/dl | | L-lysine |
| 0.55–1.66 mM/dl | | L-methionine |
| 0–3.00 mM/dl | | L-cysteine |
| 0.43–5.48 mM/dl | | L-histidine |
| 1.07–2.09 mM/dl | | L-phenylalanine |
| 0–1.32 mM/dl | | L-tyrosine |
| 0.20–0.98 mM/dl | | L-tryptophan |
| 1.46–6.76 mM/dl | | L-arginine |
| 0.81–2.71 mM/dl | | L-serine |
| 1.06–4.42 mM/dl | | L-proline |
| 1.92–4.44 mM/dl | | glycine |
| 1.30–4.66 mM/dl | | L-alanine |
| 0–2.40 mM/dl | | L-aspartic acid |
| 0.31–2.55 mM/dl | | L-glutamic acid. |

13. An amino acid solution for parenteral nutrition comprising an aqueous solution of essential and non-essential amino acids wherein the essential amino acid content consists essentially of

| | | |
|---|---|---|
| 1.03–3.30 | mM/dl | L-threonine |
| 3.03–4.13 | " | L-valine |
| 3.62–10.63 | " | L-leucine |
| 1.76–4.12 | " | L-isoleucine |
| 0.41–6.55 | " | L-lysine |
| 0.55–1.66 | " | L-methionine |
| 0–3.00 | " | L-cysteine |
| 0.43–5.48 | " | L-histidine |
| 1.07–2.09 | " | L-phenylalanine |
| 0–1.32 | " | L-tyrosine |
| 0.20–0.98 | " | L-tryptophan | and wherein said non-essential amino acids include one or more of the group consisting of L-arginine, L-serine, L-proline, glycine, L-alanine, L-aspartic acid, and L-glutamic acid.

14. An amino acid solution for parenteral nutrition comprising an aqueous solution of essential and non-essential amino acids wherein the amino acids are present in the following relative proportions as expressed in terms of moles:

| | | |
|---|---|---|
| L-threonine | 2.60 | 8.25 |
| L-valine | 7.58 | 10.32 |
| L-leucine | 9.05 | 26.58 |
| L-isoleucine | 4.40 | 10.30 |
| L-lysine | 1.02 | 16.40 |
| L-methionine | 1.38 | 4.15 |
| L-cysteine | 0 | 7.50 |
| L-histidine | 1.08 | 13.70 |
| L-phenylalanine | 2.68 | 5.22 |
| L-tyrosine | 0 | 3.30 |
| L-tryptophan | 0.50 | 2.45 |
| L-arginine | 3.65 | 16.90 |
| L-serine | 2.02 | 6.80 |
| L-proline | 2.65 | 11.05 |
| glycine | 4.80 | 11.10 |
| L-alanine | 3.25 | 11.65 |
| L-aspartic acid | 0 | 6.00 |
| L-glutamic acid | 0.78 | 6.38 |

15. An amino acid solution according to claim 14 wherein one or more of said amino acids is present in the same relative mole proportions in the form of one or more of their pharmaceutically acceptable salts, keto acid analogs, dipeptides or N-acetyl derivatives.

16. An amino acid solution according to claim 14 wherein said amino acids are present in pharmaceutically acceptable amounts.

17. An amino acid solution for parenteral nutrition comprising an aqueous solution of essential and non-essential amino acids wherein the essential amino acids are present in the following relative proportions as expressed in terms of moles:

| | | |
|---|---|---|
| L-threonine | 2.60 | 8.25 |
| L-valine | 7.58 | 10.32 |
| L-leucine | 9.05 | 26.58 |
| L-isoleucine | 4.40 | 10.30 |
| L-lysine | 1.02 | 16.40 |
| L-methionine | 1.38 | 4.15 |
| L-cysteine | 0 | 7.50 |
| L-histidine | 1.08 | 13.70 |
| L-phenylalanine | 2.68 | 5.22 |
| L-tyrosine | 0 | 3.30 |
| L-tryptophan | 0.50 | 2.45 | and wherein the molar ratio of total essential amino acids to total amino acids is in the range from 0.50 to 0.70.

18. An amino acid solution according to claim 17 wherein one or more of said amino acids is present in the same relative mole proportions in the form of one or more of their pharmaceutically acceptable salts, keto acid analogs, dipeptides or N-acetyl derivatives.

19. An amino acid solution according to claim 18 wherein said solution further comprises sufficient non-specific nonessential amino acids to provide adequate nitrogen for nutrition.

20. A method of providing nutrition to a patient for promoting growth of or maintaining lean body mass, comprising administering to said patient an aqueous amino acid solution having an amino acid content consisting essentially of amino acids in the following relative proportions as expressed in terms of moles:

| | | |
|---|---|---|
| L-threonine | 2.60 | 8.25 |
| L-valine | 7.58 | 10.32 |
| L-leucine | 9.05 | 26.58 |
| L-isoleucine | 4.40 | 10.30 |
| L-lysine | 1.02 | 16.40 |
| L-methionine | 1.38 | 4.15 |
| L-cysteine | 0 | 7.50 |
| L-histidine | 1.08 | 13.70 |
| L-phenylalanine | 2.68 | 5.22 |

| -continued | | |
|---|---|---|
| L-tyrosine | 0 | 3.30 |
| L-tryptophan | 0.50 | 2.45 |
| L-arginine | 3.65 | 16.90 |
| L-serine | 2.02 | 6.80 |
| L-proline | 2.65 | 11.05 |
| glycine | 4.80 | 11.10 |
| L-alanine | 3.25 | 11.65 |
| L-aspartic acid | 0 | 6.00 |
| L-glutamic acid | 0.78 | 6.38 |

21. An amino acid solution according to claim 20 wherein one or more of said amino acids is present in the same relative mole proportions in the form of one or more of their pharmaceutically acceptable salts, keto acid analogs, dipeptides or N-acetyl derivatives.

22. An amino acid solution according to claim 20 wherein said amino acids are present in pharmaceutically acceptable amounts.

* * * * *